United States Patent [19]

Okazaki

[11] Patent Number: 4,561,739
[45] Date of Patent: Dec. 31, 1985

[54] TRIAL SPECTACLES
[75] Inventor: Sakiho Okazaki, Suwa, Japan
[73] Assignee: Kabushiki Kaisha Suwa Seikosha, Tokyo, Japan
[21] Appl. No.: 740,311
[22] Filed: Jun. 3, 1985

Related U.S. Application Data

[63] Continuation of Ser. No. 402,887, Jul. 29, 1982, abandoned.

[30] Foreign Application Priority Data

Jul. 31, 1981 [JP] Japan ................... 56-121128

[51] Int. Cl.[4] ............................................... A61B 3/04
[52] U.S. Cl. ....................................... 351/227; 351/231
[58] Field of Search ............... 351/227, 228, 229, 230, 351/231, 204, 107, 47, 48, 57, 86, 154; 33/200

[56] References Cited

U.S. PATENT DOCUMENTS 2,337,866 12/1943 Boughton et al. ................... 351/227
4,252,419 2/1981 Padula, II et al. ................... 351/204

FOREIGN PATENT DOCUMENTS 160680 3/1921 United Kingdom ................... 33/200

Primary Examiner—Rodney B. Bovernick
Assistant Examiner—P. M. Dzieszynski
Attorney, Agent, or Firm—Blum, Kaplan, Friedman, Silberman & Beran

[57] ABSTRACT

A pair of trial spectacles for allowing a wearer to test the feeling and effect of a pair of spectacles and lenses before an actual pair is constructed. The trial spectacles include a frame member adapted to be supported on the face of a wearer having at least a first eye rim portion positioned in front of one of the eyes of wearer when the frame member is supported on the face of the wearer. The first rim portion is adapted to removably support a first lens. The first lens is horizontally slidable in the first portion so that the first lens can be horizontally adjusted to meet the wearer's visual requirements.

8 Claims, 3 Drawing Figures

TRIAL SPECTACLES

This is a continuation of application Ser. No. 402,887, filed July 29, 1982, now abandoned.

BACKGROUND OF THE INVENTION

The present invention relates generally to a pair of trial spectacles and, in particular, to a pair of spectacles for testing the feeling and effect of various kinds of ophthalmic lenses at the time of wearing so that a wearer with a reduced power of accommodation can test whether multifocal lenses are suitable prior to constructing an actual pair of spectacles and lenses for permanent use.

Multifocal lenses for use in spectacles or eyeglasses may include a bifocal lens, a double bifocal lens, a trifocal lens, a progressive multifocal lens or the like. These respective multifocal lenses include various lenses designed for use by a wearer having a reduced power of accommodation. Such lenses prove convenient for wearers with a reduced power of accommodation since such a wearer can see both far and near objects clearly with a single lens. However, such types of multifocal lenses have several shortcomings. For example, a wearer may experience a jumping of image at the dividing line between the various lenses of the bifocal and trifocal lenses and may also experience shaking and blurring of the image in the peripherial portion of the progressive multifocal lens.

It proves difficult for a wearer to fully understand and appreciate the optical characteristics of the types of multifocal lenses under discussion when only an oral or written explanation of the effects and shortcomings of the lenses is made. Thus, it often happens that the wearer cannot realize the above-described shortcomings until the wearer actually tries a pair of spectacles constructed to meet his particular optical specifications and requirements. A wearer may think that he could understand the optical characteristics by explanation and agrees that a pair of spectacles having multifocal lenses should be made, but finds that he cannot endure the shortcomings of the spectacles and lenses when he actually receives and wears the pair of spectacles. Once having been constructed to the wearer's particular optical prescription and the wearer finds the multifocal lenses in the pair of spectacles unsuitable for him, such pair of spectacles and lenses cannot be utilized for other wearers having different optical prescriptions and requirements.

It is therefore desirable for a wearer to wear a pair of spectacles having multifocal lenses on a trial basis in order to understand its characteristics through his own experience before constructing the actual pair of spectacles and lenses for permanent use by the wearer. Trial spectacle frames and trial lenses have been conventionally used in order for a user to wear them on a trial basis. However, heretofore, the main object of utilizing the trial frames and lenses was to allow the wearer's ophthalmologist or optometrist to determine the focal power of the ophtalmic lenses necessary for that particular wearer. Accordingly, the aperture of trial lenses is relatively small in order to reduce the weight thereof even when three or four lenses, for example, are overlapped in the trial frame, since it is sufficient that only the central front view can be seen by the wearer. The effective diameters of trial lenses utilized in trial spectacle frames are generally less than 35 mm. In this regard, see Moss, A Demonstration Kit for Progressive Addition Lenses, Review of Optometry/May, 1978.

However, in the case of multifocal lenses, the portion of the lens for near vision is generally positioned below the center of the lens. In the progressive multifocal lenses, shaking of the image and blur distinctly appear not in the center of the lens but in the peripheral portions thereof. Thus, in the case of testing the feeling and effect of various kinds of multifocal lenses at the time of wearing, it is difficult for a user to understand the optical characteristics of the multifocal lenses even by utilizing the conventional trial frame and trial lenses whose aperture is small, since an important portion of the lens for understanding the optical characteristics of the multifocal lenses is not available in convention trial lenses. In addition, in the case of using multifocal lenses, it proves most important to adjust the fixed point or "fitting point" on the lens, which is generally at or near the optical center of the lens, with the center of the wearer's pupil.

Thus, when a wearer is looking at distant objects, it is necessary that the fitting point of the lens acccurately coincide with the center of the wearer's pupil in a front view. Accordingly, a trial frame for testing needs to have the function where the lens can be horizontally and vertically adjusted. In addition, since conventional trial frames are heavy, they will tend to slip down the wearer's nose or the wearer will feel uncomfortable because of the weight of the pair of spectacles. It is therefore difficult for a wearer to accurately judge whether a pair of spectacles having multifocal lenses are right for him since he cannot accurately judge the feeling at the time of wearing. In addition, as the conventional trial lenses do not have any means for accurately showing the position of the fitting point, an accurate adjustment cannot be made.

Accordingly, a pair of trial spectacles which allows a wearer to test whether a pair of spectacles having multifocal lenses is suitable, which provides the same characteristics as an actual pair of spectacles with multifocal lenses is desired.

SUMMARY OF THE INVENTION

Generally speaking, in accordance with the present invention, a pair of trial spectacles which allow a wearer to test the feeling and effect of the spectacles and lenses prior to construction of a permanent pair of spectacles, is provided. The spectacles include a frame member adapted to be supported on the face of a wearer having at least a first rim portion positioned in front of one of the eyes of the wearer when the frame member is supported on the wearer's face. A first lens is adapted to be removably supported in the first rim portion. The first rim portion is constructed to permit horizontal adjustment of the lens when supported in the rim portion. The lens can be horizontally positioned in the rim to conform to a wearer's visual requirements.

In a preferred embodiment, the spectacles include two eye rim portions corresponding to the eyes of a wearer. A lens is adapted to be removably supported in each rim portion and can be horizontally adjusted in the rim portion to meet the wearer's visual requirements. The spectacles also include a nose pad adapted to rest on the bridge of a wearer's nose which can be adjusted in the vertical direction for vertically adjusting the lenses with respect to the wearer's visual requirements. The lenses may include a mark or hole at or near the fitting point of the lenses at a substantially central portion thereof so that vertical and horizontal positioning of the lenses can be made to insure that the mark is properly positioned with respect to the pupils of the wearer's eyes.

Accordingly, it is an object of the present invention to provide an improved pair of trial spectacles.

Another object of the present invention is to provide a pair of spectacles which allows a user to test the feeling and effect of a pair of spectacles having multifocal lenses before a permanent pair of spectacles and lenses is constructed.

A further object of the invention is to provide an improved pair of trial spectacles for testing the feeling and effect at the time of wearing which can be accurately and simply adjusted and which allows the wearer to appreciate how an actual pair of spectacles having multifocal lenses will feel and perform.

A still further object of the invention is to provide an improved pair of spectacles for testing the feeling and effect at the time of wearing having almost the same outer shape as that of an ordinary spectacle frame wherein the lenses can be readily exchanged and the position of the lenses can be accurately and simply adjusted in both the horizontal and vertical direction in order to coincide the wearer's pupillary center with the fitting point of the lenses.

Still other objects and advantages of the invention will in part be obvious and will in part be apparent from the specification.

The invention accordingly comprises the features of construction, combination of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
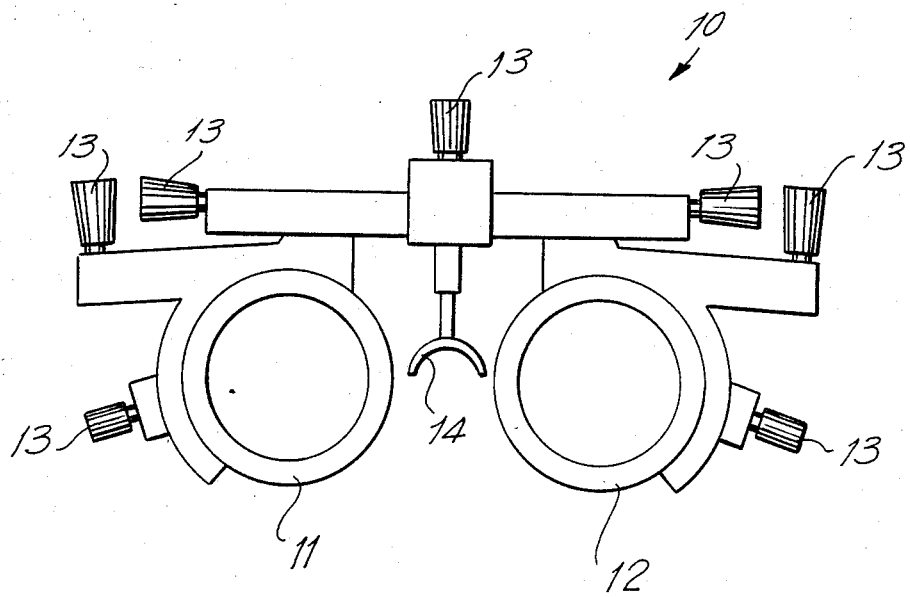
FIG. 1 is a front plan view of a trial frame of a pair of spectacles constructed in accordance with the prior art.

Reference is first made to FIG. 1 which depicts a trial frame, generally indicated at 10, constructed in accordance with the prior art. Trial frame 10 includes round rim portions 11 and 12 adapted to support round lenses therein. A plurality of adjustment knobs 13 are provided for adjusting trial frame 10 to correspond to the wearer's visual requirements. A nose pad 14 is utilized to support trial frame 10 on the bridge of the nose of the wearer so that eye rims 11 and 12 are positioned in front of the right and left eyes, respectively, of the wearer.

Conventional trial frames, such as trial frame 10, are utilized to permit determination of the particular focal power of ophthalmic lenses suitable for use by the wearer. In determining the focal power, it is not necessary to utilize full sized and shaped lenses. Thus, the aperture of the trial lenses to be utilized in trial frame 10 are relatively small in order to reduce the weight of the trial frame even when three or four lenses are overlapped in rim portions 11 and 12 of trial frame 10. It is sufficient in trial frame 10 that only the central front view through the lenses can be seen. The effective diameters of trial lenses to be utilized in trial frame 10 are less than 35 mm.

Such conventional trial lenses do not allow the wearer to experience the feeling and effect of the actual lenses which will be constructed to meet the wearer's visual requirements after the proper focal power is determined. The actual characteristics of lenses for testing the feeling and the effect at the time of wearing cannot be understood by the wearer since the lenses are too small, the area of the lenses being generally less than half of the actual lenses which are to be constructed for the wearer. In the case of multifocal lenses, characteristics of the lenses, such as the near visual portion appearing in the lower part of the lens, or shaking of the image and blur in the peripheral portions of progressive multifocal lenses, appear away from the center of the lenses. However, the portion away from the center of the lenses is not present in the round lenses utilized in the trial frame 10 depicted in FIG. 1. In addition, trial frame 10 feels uncomfortable since it is relatively heavy. Accordingly, trial frame 10 is not suitable for a wearer to experience the true feeling and effect of an actual pair of trial spectacles and multifocal lenses.

Figure 2:
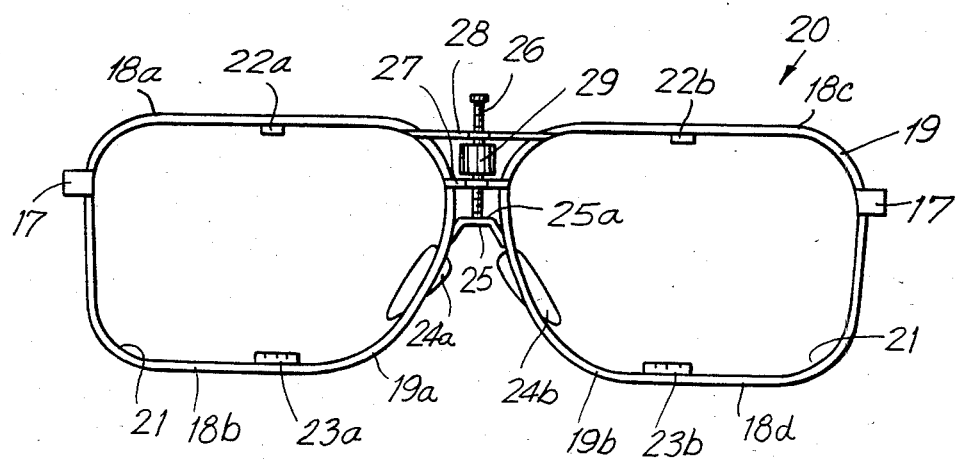
FIG. 2 is a front plan view of a pair of trial spectacles for testing the feeling and effect at the time of wearing constructed in accordance with a preferred embodiment of the present invention.
Figure 3:
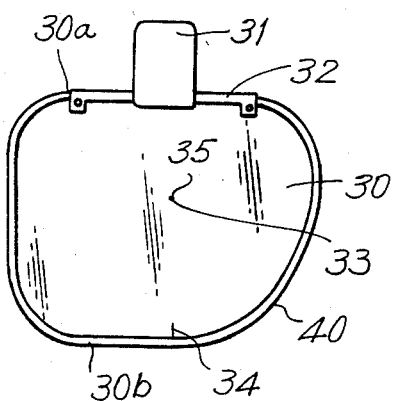
FIG. 3 is a front plan view of a trial lens for use in the pair of trial spectacles is depicted in FIG. 2 constructed in accordance with the present invention.

Reference is now made to FIG. 2 which depicts a pair of trial spectacles, generally indicated at 20, for allowing a wearer to test the feeling and effect of a pair of spectacles with lenses such as multifocal lenses at the time of wearing, constructed in accordance with the present invention. FIG. 3 depicts a lens 30 for the right eye of a wearer for use in spectacles 20 in FIG. 2, constructed in accordance with the present invention. A similarly constructed lens is provided for the wearer's left eye. Frame 19 of trial spectacles 20 is designed in such a way as to be substantially similar to an actual spectacle frame for ordinary, daily use. A plurality of lenses 30, as depicted in FIG. 3, for both the right and left eyes are constructed having different focal powers. The lenses whose focal power is suitable for the wearer are selected and utilized in trial frame 19 as described below.

As depicted in FIG. 2, frame 19 includes a first eye rim portion 19a for the wearer's right eye and a second eye rim portion 19b for the wearer's left eye. The upper portion 18a of first rim portion 19a is substantially parallel to the lower portion 18b of first eye rim portion 19a. The upper portion 18c of second eye rim portion 19b is substantially parallel to the lower portion 18d of second eye rim portion 19b. It is noted that the sectional shape of eye rim portions 19a and 19b are the same as that of an ordinary spectacle frame. Both eye rim portions 19a and 19b includes a V-shaped groove 21 therearound for receiving a lens 30.

Stoppers 22a and 22b are braised on the upper portions 18a and 18c, respectively, of eye rims 19a and 19b and act to hold lenses 30 which are supported therein. Scale plates 23a and 23b are braised on the lower portions 18b and 18d, respectively, of eye rims 19a and 19b and cooperate with stoppers 22a and 22b, respectively, to hold lenses 30 therein. The position of lenses 30 can be determined by the scale on scale plates 23a and 23b when the wearer's pupillary distance is previously known. Nose pads 24a and 24b are coupled to a V-shaped nose pad arm 25. An adjustment screw 26 is braised at the top 25a of pad arm 25 and is screwed into an adjustment roller 29 which is placed between bridges 27 and 28 of frame 19. Nose pads 24a and 24b can be vertically adjusted to vertically adjust frame 19 when positioned on the face of a wearer by rotating adjustment roller 29. Temple members 17 are secured to eye rims 19a and 19b and extend back to the wearer's ears for allowing proper support of trial spectacles 20 on the wearer's face.

Lens 30 depicted in FIG. 3 includes an upper portion 30a which is substantially parallel to a lower portion 30b thereof. A bevel edge 40 is provided around the periphery of spectacle lens 30 which corresponds to the V-shaped groove 21 in rim portions 19a and 19b. A name plate 31 is secured to the upper part 30a of lens 30 by means of a coupling member 32. The lens type, focal power and the like can be indicated on name plate 31. In addition, name plate 31 can be utilized to hold lens 30 without having to touch and possibly mar lens 30.

A small and shallow hole 35 is made at or near fitting point 33 of lens 30. The center of the wearer's pupil can readily be coincided with fitting point 33 since hole 35 is seen as clear and white with a colored pupil for the background in the front view. This allows for proper positioning of lens 30 with respect to the wearer's eyes. It is important that hole 35 not be too large since it will then be recognizable by the wearer and will interfere with his testing of the feeling and effect of the lenses. If hole 35 is too small, it will be difficult to distinguish the hole. Therefore, it is desirable that the diameter of the hole be between 0.15 and 0.5 mm. A fine vertical line 34 is provided under fitting point 33 and is set to correspond to the scale on scale plates 23a and 23b so as to correspond to the wearer's pupillary distance in case it is previously known.

With respect to the outer shape of lens 30, it is again noted that the upper portion 30a and lower portion 30b thereof are substantially parallel. The longitudinal dimension of lens 30 is determined in such a way that lens 30 fits snugly in eye rim portion 19a, the same being true for a similar lens constructed for use in rim portion 19b. The overall shape of lens 30 is substantially the same as that of eye rim 19a and the transverse width of lens 30 is smaller than that of eye rim 19a. Thus, lens 30 can be horizontally slid and adjusted between upper and lower portions 18a and 18b of eye rim 19a. As depicted in FIG. 3, for example, the longitudinal dimension of lens 30 may be 40 mm and the transverse width 50 mm. The transverse width of rim 19a in FIG. 2 would then be 58 mm.

It will now be explained how to utilize trial spectacles 20 for testing the feeling and effect at the time of wearing in accordance with the present invention. First, lenses whose focal power is suitable for the right and left eyes of the wearer who is going to test the feeling and effect at the time of wearing in accordance with the eye prescription of the wearer, are selected. The selected lenses are placed in the proper eye rim portion 19a and 19b of frame 19. At this time, it is desirable to hold name plate 31 and push the lower part 18b of eye rim 19a or to softly push apart both sides 18a and 18b of rim 19a and to open eye rim 19a to allow the lens to be positioned therein.

In case the wearer's pupillary distance is previously determined, line 34 on lens 30 is set to the proper scale dimension on scale plate 23 which corresponds to the wearer's pupillary distance. The ophthalmologist or optometrist who is fitting the lenses frontally faces the wearer and adjusts the spectacles in a way so that fitting point 33 determined by mark or hole 35 coincides with the wearer's pupil centers. The spectacles can be vertically adjusted by rotating adjustment roller 29 and horizontally adjusted by holding name plate 11 and sliding the lens within eye rim 19a in the horizontal direction. Thus, in accordance with the present invention, a pair of trial spectacles for testing the feeling and effect at the time of wearing which has an outer shape and weight suitable for daily use and by which the feeling and effect of given lenses such as multifocal lenses can be accurately tested by simple operation, can be provided.

It is noted that the present invention should not be construed as limited to the above described construction. For example, as described above, the lens has parallel upper and lower portions. However, it is not necessary that the outer shape of the upper and lower portions of the lens be substantially parallel. For example, a curved line which curves to the inside can be utilized. In such a case, the lens touches the eye rim at 4 points only, but the purpose of sliding the lens in the horizontal direction in the eye rim can be sufficiently attained. Such a lens has the advantage that it can be readily set and the frame easily adjusted. In addition, the scale on scale plate 23 can be directly notched on the eye rim in order to set the wearer's pupillary distance, although a separate scale plate affixed to the eye rims is utilized in the present invention as described above. Moreover, as described above, a hole is made at or near the fitting point of the lens itself, but there is also a method of making a mark by printing and the like. With respect to the position of the fitting point, there is a method wherein two marks are made at the same distance from the fitting point on both sides of the fitting point.

According to the present invention, a pair of trial spectacles suitable for everyday wear by the wearer to enable the wearer to test the feeling and effect the spectacles and lenses is provided. The spectacles are adaptable for use by a plurality of wearers with only a lens selection being required. Where multifocal lenses are utilized, the wearer obtains actual experience in utilizing the multifocal lenses and can determine whether they are suitable for him. The lenses are readily horizontally adjustable in the eye rim portions of the trial frame and the entire frame can be vertically adjusted to insure proper positioning of the lenses.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A pair of trial spectacles comprising a frame member adapted to be supported on the face of a wearer having a first rim portion positioned in front of one of the eyes of the wearer and a second rim portion, said frame member including bridge means for fixedly coupling said first rim portion to said second rim portion, said second rim portion being positioned in front of the other eye of the wearer when said frame member is supported on the face of the wearer, a first lens slidably, removably supported in said first rim portion, said first lens being horizontally slidable in said first rim portion so that said first lens can be horizontally adjusted to meet the wearer's visual requirements, a second lens slidably, removably supported in said second rim portion, said second lens being horizontally slidable in said second rim portion so that said second lens can be horizontally adjusted to meet the wearer's visual requirements, said first and second lenses each including an upper portion and a lower portion essentially parallel to said upper portion, said first and second rim portions each including an upper portion and a lower portion essentially parallel to said upper portion, said first and second lenses being horizontally slidable between the respective upper and lower portions of said first and second rim portions, respectively, said first and second lenses having a smaller transverse width than the respective widths of said first and second rim portions to permit horizontal sliding adjustment of said first and second lenses in said first and second rim portions, respectively, said first and second lenses each having a longitudinal length essentially equal to the distance between the upper and lower portions of said first and second rim portions, respectively.

2. The pair of trial spectacles as claimed in claim 1, wherein said first lens includes a fitting point, said first lens having first indicating means thereon for indicating the position of said fitting point so that said first lens can be properly positioned in front of wearer's eye, said second lens including a fitting point, said second lens having second indicating means for indicating the position of said fitting point of said second lens so that said second lens can be properly positioned in front of the wearer's other eye.

3. The pair of trial spectacles as claimed in claim 1, wherein said frame member includes positioning means for permitting vertical adjustment of said frame member on the wearer's face so that said first and second lenses, when supported in said first and second rim portions, respectively, can be properly positioned in front of the wearer's eyes to meet the visual requirements of the wearer.

4. The pair of trial spectacles as claimed in claim 1, wherein said first and second rim portions include a first and second scale means, respectively, for indicating distance, said first and second scale means allowing for horizontal positioning of said first and second lenses in said first and second rim portions, respectively, when the pupillary distance of the wearer is known.

5. The pair of trial spectacles as claimed in claim 3, wherein said first scale means is braised to said lower portion of said first rim portion and said second scale means is braised to said lower portion of said second rim portion.

6. The pair of trial spectacles as claimed in claim 5, wherein said first and second lens each include a mark thereon for corresponding said first and second lenses to said first and second scale means, respectively.

7. The pair of trial spectacles as claimed in claim 4, wherein said frame includes a nose pad means supported on said bridge means for supporting said frame on the nose of a wearer, said positioning means selectively adjusting the position of said nose pad means with respect to said bridge means so that the vertical position of said frame member can be adjusted when on the face of a wearer.

8. The pair of trial spectacles as claimed in claim 2, wherein said first indicating means is a mark on said first lens proximate said fitting point, said mark having a diameter no greater than 0.5 mm, said second indicating means being a mark on said second lens proximate said fitting part, said mark having a diameter no greater than 0.5 mm.

* * * * *